(12) United States Patent
Josch et al.

(10) Patent No.: US 10,370,310 B2
(45) Date of Patent: Aug. 6, 2019

(54) METHOD FOR PREPARING 1,3-BUTADIENE FROM N-BUTENES BY OXIDATIVE DEHYDROGENATION

(71) Applicants: BASF SE, Ludwigshafen am Rhein (DE); Linde AG, Munich (DE)

(72) Inventors: Jan Pablo Josch, Ludwigshafen am Rhein (DE); Georgios Karanikoulis, Ludwigshafen am Rhein (DE); Oliver Hammen, Ludwigshafen am Rhein (DE); Claudia Mossbacher, Ludwigshafen am Rhein (DE); Ulrike Wenning, München (DE); Anton Wellenhofer, München (DE); Christine Toegel, München (DE); Hendrik Reyneke, München (DE)

(73) Assignees: BASF SE (ISENBRUCK BÖSL HÖRSCHLER LLP), Ludwigshafen am Rhein (DE); Linde AG, Munich (DE)

(*) Notice: Subject to any disclaimer, the term of this patent is extended or adjusted under 35 U.S.C. 154(b) by 0 days.

(21) Appl. No.: 16/069,553

(22) PCT Filed: Jan. 11, 2017

(86) PCT No.: PCT/EP2017/050438
§ 371 (c)(1),
(2) Date: Jul. 12, 2018

(87) PCT Pub. No.: WO2017/121739
PCT Pub. Date: Jul. 20, 2017

(65) Prior Publication Data
US 2019/0016650 A1 Jan. 17, 2019

(30) Foreign Application Priority Data
Jan. 13, 2016 (EP) .................................. 16151045

(51) Int. Cl.
*C07C 5/48* (2006.01)
*C07C 7/06* (2006.01)
(Continued)

(52) U.S. Cl.
CPC ............... *C07C 5/48* (2013.01); *C07C 7/005* (2013.01); *C07C 7/04* (2013.01); *C07C 7/06* (2013.01);
(Continued)

(58) Field of Classification Search
CPC .. C07C 5/48; C07C 7/005; C07C 7/04; C07C 7/08; C07C 7/11
See application file for complete search history.

(56) References Cited

U.S. PATENT DOCUMENTS 3,932,551 A  1/1976  Grasselli et al.
3,956,181 A  5/1976  Grasselli et al.
(Continued)

FOREIGN PATENT DOCUMENTS

DE  2440329 A1  3/1975
DE  2447825 A1  8/1975
(Continued)

OTHER PUBLICATIONS

Database WPI, Week 201107, Thomson Scientific, London, GB; AN 2011-A58751, XP002759141.
(Continued)

*Primary Examiner* — Youngsul Jeong
*Assistant Examiner* — Jason Y Chong
(74) *Attorney, Agent, or Firm* — Drinker Biddle & Reath LLP

(57) ABSTRACT

The invention relates to a method for producing butadiene from n-butenes having the steps:
A) providing a feed gas stream a comprising n-butenes;
B) feeding the feed gas stream a comprising the n-butenes and an oxygen-comprising gas into at least one oxidative dehydrogenation zone and oxidatively dehydrogenating n-butenes to butadiene, wherein a product gas stream b
(Continued)

comprising butadiene, unreacted n-butenes, steam, oxygen, low-boiling hydrocarbons, high-boiling minor components, possibly carbon oxides and possibly inert gases is obtained;

Ca) cooling the product gas stream b by contacting it with a refrigerant and condensing at least a part of the high-boiling minor components;

Cb) compressing the remaining product gas stream b in at least one compression stage, wherein at least one aqueous condensate stream c1 and a gas stream c2 comprising butadiene, n-butenes, steam, oxygen, low-boiling hydrocarbons, possibly carbon oxides and possibly inert gases are obtained;

Da) separating off non-condensable and low-boiling gas components comprising oxygen, low-boiling hydrocarbons, possibly carbon oxides and possibly inert gases as gas stream d2 from the gas stream c2 by absorbing the $C_4$ hydrocarbon-comprising butadiene and n-butenes in an absorbent, wherein an absorbent stream loaded with $C_4$ hydrocarbons and the gas stream d2 are obtained, and Db) subsequent desorption of the $C_4$ hydrocarbons from the loaded absorbent stream in a desorption column, wherein a $C_4$ product gas stream d1 is obtained, wherein a polymerization inhibitor is added in step Db) at the column head of the desorption column.

8 Claims, 1 Drawing Sheet

(51) Int. Cl.
*C07C 7/08* (2006.01)
*C07C 7/11* (2006.01)
*C07C 7/00* (2006.01)
*C07C 7/04* (2006.01)

(52) U.S. Cl.
CPC ................ *C07C 7/08* (2013.01); *C07C 7/11* (2013.01); *C07C 2521/06* (2013.01); *C07C 2523/31* (2013.01); *C07C 2523/86* (2013.01); *C07C 2523/88* (2013.01); *C07C 2523/881* (2013.01)

(56) References Cited

U.S. PATENT DOCUMENTS

| | | |
|---|---|---|
| 3,991,039 A | 11/1976 | Gunter et al. |
| 4,162,234 A | 7/1979 | Grasselli et al. |
| 4,336,409 A | 6/1982 | Yamamoto et al. |
| 4,397,771 A | 8/1983 | Grasselli et al. |
| 4,423,281 A | 12/1983 | Yamamoto et al. |
| 4,424,141 A | 1/1984 | Grasselli et al. |
| 4,547,615 A | 10/1985 | Yamamoto |
| 9,957,208 B2 | 5/2018 | Grune et al. |
| 2012/0130137 A1 | 5/2012 | Orita et al. |
| 2014/0200381 A1* | 7/2014 | Josch ................. C07C 7/05 585/621 |
| 2015/0126788 A1* | 5/2015 | Takagaki ............ C07C 7/10 585/326 |
| 2016/0347686 A1 | 12/2016 | Grune et al. |
| 2017/0334809 A1 | 11/2017 | Grune et al. |
| 2018/0002254 A1 | 1/2018 | Josch et al. |
| 2018/0105479 A1 | 4/2018 | Josch et al. |
| 2018/0282246 A1 | 10/2018 | Ungelenk et al. |

FOREIGN PATENT DOCUMENTS

| | | |
|---|---|---|
| DE | 2530959 A1 | 2/1976 |
| DE | 2600128 A1 | 7/1976 |
| JP | 2010090083 A | 4/2010 |
| JP | 2011001341 A | 1/2011 |
| JP | 2011006381 A | 1/2011 |
| JP | 2011132218 A | 7/2011 |
| JP | 2012240963 A | 12/2012 |
| WO | WO-2014111409 A1 | 7/2014 |
| WO | WO-2016150738 A1 | 9/2016 |
| WO | WO-2016150940 A1 | 9/2016 |
| WO | WO-2016151033 A1 | 9/2016 |
| WO | WO-2016151074 A1 | 9/2016 |

OTHER PUBLICATIONS

International Search Report for PCT/EP2017/050438 dated Mar. 29, 2017.
Written Opinion of the International Searching Authority for PCT/EP2017/050438 dated Mar. 29, 2017.
U.S. Appl. No. 15/780,725.
U.S. Appl. No. 16/069,553.

* cited by examiner

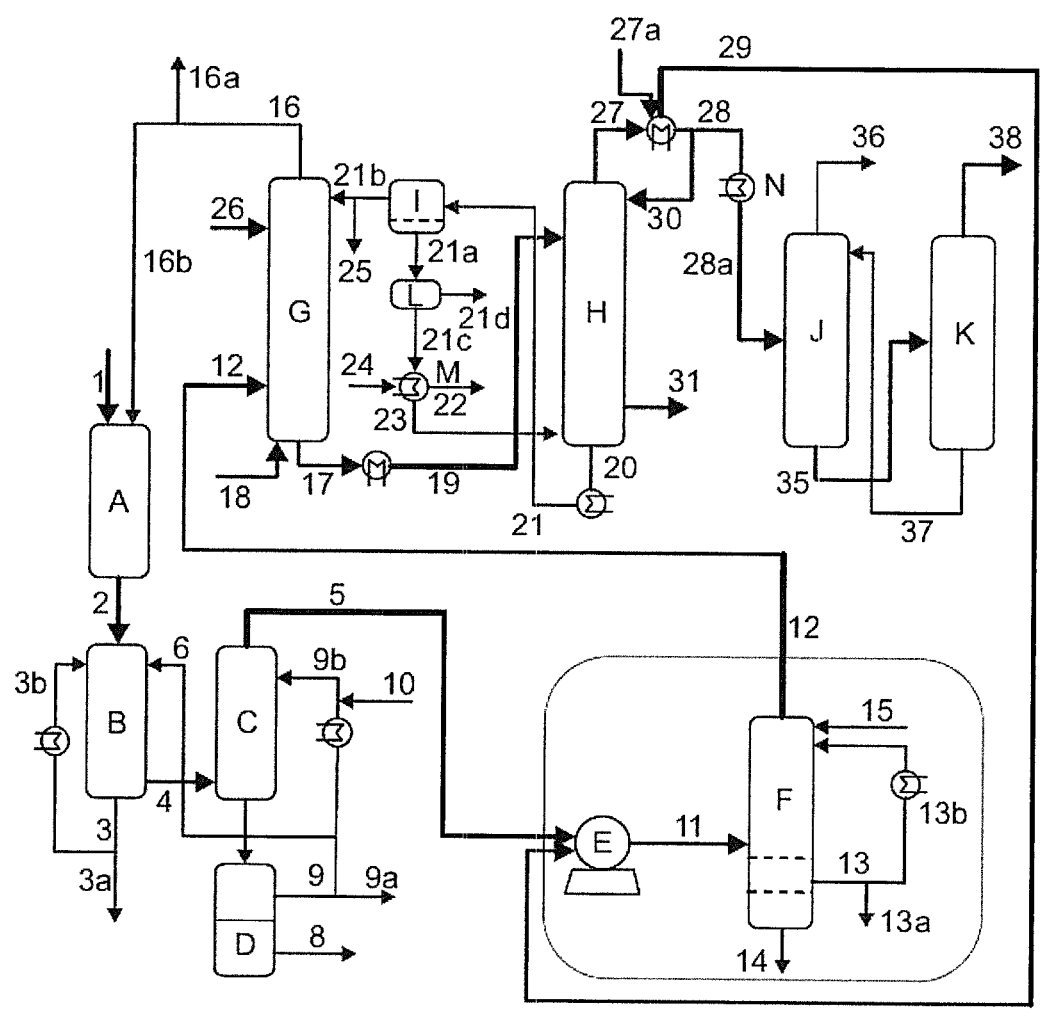

US 10,370,310 B2

METHOD FOR PREPARING 1,3-BUTADIENE FROM N-BUTENES BY OXIDATIVE DEHYDROGENATION

CROSS-REFERENCE TO RELATED APPLICATIONS

This application is a national stage application (under 35 U.S.C. § 371) of PCT/EP2017/050438, filed Jan. 11, 2017, which claims benefit of European Application No. 16151045.8, filed Jan. 13, 2016, both of which are incorporated herein by reference in their entirety.

The invention relates to a method for producing 1,3-butadiene from n-butenes by oxidative dehydrogenation (ODH), in which a polymerization inhibitor is added in the work-up part.

Butadiene is an important basic chemical and is used, for example, for producing synthetic rubbers (butadiene homopolymers, styrene-butadiene rubber or nitrile rubber) or for producing thermoplastic terpolymers (acrylonitrile-butadiene-styrene copolymers). Butadiene is additionally reacted to form sulfolane, chloroprene and 1,4-hexamethylenediamine (via 1,4-dichlorobutene and adipodinitrile). By dimerizing butadiene, in addition, vinylcyclohexene can be generated, which can be dehydrogenated to form styrene.

Butadiene can be produced by the thermal cracking (steam cracking) of saturated hydrocarbons, customarily starting from naphtha as raw material. In the steam cracking, of naphtha, a hydrocarbon mixture of methane, ethane, ethene, acetylene, propane, propene, propyne, allene, butanes, butenes, butadiene, butynes, methylallene, $C_5$— and higher hydrocarbons is produced.

Butadiene can also be obtained by oxidative dehydrogenation of n-butenes (1-butene and/or 2-butene). The starting mixture used for the oxidative dehydrogenation (oxy dehydrogenation, ODH) of n-butenes to form butadiene can be any desired mixture containing n-butenes. For example, a fraction can be used that, as main component, comprises n-butenes (1-butene and/or 2-butene) and was obtained from the $C_4$ fraction of a naphtha cracker by separating off butadiene and isobutene. In addition, gas mixtures can be used as starting gas, which mixtures comprise 1-butene, cis-2-butene, trans-2-butene or mixtures thereof, and were obtained by dimerizing ethylene. In addition, as starting gas, gas mixtures comprising n-butenes can be used, which mixtures were obtained by fluid catalytic cracking (FCC).

Methods for the oxidative dehydrogenation of butenes to butadiene are known in principle. Such methods frequently comprise the following steps:

A) providing a feed gas stream a comprising n-butenes;
B) feeding the feed gas stream a comprising n-butenes and an oxygen-comprising gas n-butenes to butadiene, wherein a product gas stream b comprising butadiene, unreacted n-butenes, steam, oxygen, low-boiling hydrocarbons, high-boiling minor components, possibly carbon oxides and possibly inert gases is obtained;
Ca) cooling the product gas stream b by contacting it with a refrigerant and condensing at least a part of the high-boiling minor components;
Cb) compressing the remaining product gas stream b in at least one compression stage, wherein at least one aqueous condensate stream c1 and a gas stream c2 comprising butadiene, n-butenes, steam, oxygen, low-boiling hydrocarbons, possibly carbon oxides and possibly inert gases are obtained;
Da) separating off non-condensable and low-boiling gas components comprising oxygen, low-boiling hydrocarbons, possibly carbon oxides and possibly inert gases as gas stream d2 from the gas stream c2 by absorbing the $C_4$ hydrocarbon-comprising butadiene and n-butenes in an absorbent, wherein an absorbent stream loaded with $C_4$ hydrocarbons and the gas stream d2 are obtained, and
Db) subsequent desorption of the $C_4$ hydrocarbons from the loaded absorbent stream in a desorption column, wherein a $C_4$ product gas stream d1 is obtained.

US 2012/0130137A1, for example, describes a method for the oxidative dehydrogenation of butenes to butadiene, using catalysts which comprise oxides of molybdenum, bismuth and generally further metals.

In paragraph [0122], the problems of byproducts are also referred to. In particular phthalic anhydride, anthraquinone and fluorenone are mentioned, which are typically present in the product gas at concentrations from 0.001 to 0.10% by volume. In US 2012/0130137A1, paragraph [0124] to [0126], it is recommended to cool the hot reactor discharge gases directly to firstly 5 to 100° C. by contacting them with a coolant liquid (quench tower). Water or aqueous alkali solutions are mentioned as coolant liquids. The problems of blockages in the quench due to high-boilers from the product gas or due to polymerization products of high-boiling byproducts from the product gas are explicitly mentioned as coolant liquids, for which reason it is said to be advantageous that high-boiling byproducts are discharged as little as possible from the reaction part into the cooling part (quench). Separating off isobutene from the decomposition product thereof, methacrolein, from acetaldehyde or from acrolein is not mentioned.

In JP 2011-001341A, a two-stage cooling is described for a method for the oxidative dehydrogenation of alkenes to conjugated alkadienes. In this case, the product discharge gas of the oxidative dehydrogenation is first adjusted to a temperature between 300 and 221° C. and then further cooled to a temperature between 99 and 21° C. In paragraphs [0066] f., it is described that, to set the temperature between 300 and 221° C., heat exchangers are preferably used, wherein, however, a part of the high-boilers could also precipitate out of the product gas in said heat exchangers. In JP2011-001341A, therefore, an occasional washing out of deposits from the heat exchangers using organic or aqueous solvents is described. As solvents, for example, aromatic hydrocarbons such as toluene or xylene, or an alkaline aqueous solvent such as, for example, the aqueous solution of sodium hydroxide are described. In order to avoid too-frequent shutting down of the method for cleaning the heat exchangers, in JP 2011-001341A, a structure having two parallel-arranged heat exchangers is described, which are each operated or purged alternately (what is termed A/B procedure). A separation from isobutene or from the decomposition product thereof, methacrolein, of from acetaldehyde and acrolein is not mentioned.

JP 2011-132218 restricts the isobutene content in the feed, since it is known that isobutene forms oxygenates. Separating off the oxygenates, however, is not described.

JP 2012240963 describes a method for butadiene production in which the $C_4$ hydrocarbon-comprising gas stream is contacted with an absorbent b in an absorbent stage b', in order to absorb the $C_4$ components.

JP 2010-090083 limits the amount of aldehydes and also discloses in table 1 the formation of methacrolein, but makes no proposal on separating it off.

Isobutene is present in virtually all $C_4$ hydrocarbon streams that can be used for the ODH process. In particular, $C_4$ hydrocarbon streams from FC crackers comprise isobutene in amounts of up to 15% by volume. The isobutene entering the ODH reactor is, depending on the catalyst used and the reaction conditions, converted to methacrolein by approximately 50%. Said methacrolein accumulates in the circuit stream of the absorption/desorption part of the $C_4$ hydrocarbon removal and can cause side reactions such as oligomerizations and polymerizations, deposits on the column internals, and in particular on evaporators and condensers, and also an impairment of the separation efficiency.

It has been found that the minor components present in the product gas stream of the ODH reactor initiate and promote polymer formation in regions of the downstream work-up stages in which high concentrations of $C_4$ hydrocarbons are present.

In JP 2011-006381 A, the risk of peroxide formation in the work-up part of a method for producing conjugated alkadienes is addressed. To solve this problem, the addition of polymerization inhibitors to the absorption solutions of the $C_4$ hydrocarbon removal and setting a maximum peroxide content of 100 ppm by weight by heating absorption solutions is described.

The object of the invention is to provide an improved method for producing butadiene by oxidative dehydrogenation of n-butenes and subsequent work-up of the product gas stream comprising $C_4$ hydrocarbons and minor components, which method provides a remedy to the disadvantages described above. In particular, a method is to be provided in which polymer formation is minimized during the removal of the $C_4$ hydrocarbons from the product gas stream of the ODH reactor in the work-up part of the method.

BRIEF DESCRIPTION OF THE DRAWINGS

FIG. 1 shows an embodiment of the method according to the invention.

The object is achieved by a method for producing butadiene from n-butenes having the steps:
A) providing a feed gas stream a comprising n-butenes;
B) feeding the feed gas stream a comprising n-butenes and an oxygen-comprising gas into at least one oxidative dehydrogenation zone and oxidatively dehydrogenating n-butenes to butadiene, wherein a product gas stream b comprising butadiene, unreacted n-butenes, steam, oxygen, low-boiling hydrocarbons, high-boiling minor components, possibly carbon oxides and possibly inert gases is obtained;
Ca) cooling the product gas stream b by contacting it with a refrigerant and condensing at least a part of the high-boiling minor components;
Cb) compressing the remaining product gas stream b in at least one compression stage, wherein at least one aqueous condensate stream c1 and a gas stream c2 comprising butadiene, n-butenes, steam, oxygen, low-boiling hydrocarbons, possibly carbon oxides and possibly inert gases are obtained;
Da) separating off non-condensable and low-boiling gas components comprising oxygen, low-boiling hydrocarbons, possibly carbon oxides and possibly inert gases as gas stream d2 from the gas stream c2 by absorbing the $C_4$ hydrocarbon-comprising butadiene and n-butenes in an absorbent, wherein an absorbent stream loaded with $C_4$ hydrocarbons and the gas stream d2 are obtained, and
Db) subsequent desorption of the $C_4$ hydrocarbons from the loaded absorbent stream in a desorption column, wherein a $C_4$ product gas stream d1 is obtained,
wherein a polymerization inhibitor is added in step Db) at the column head of the desorption column.

Generally, a top condenser is situated at the column head of the desorption column. Preferably, the polymerization inhibitor is added in the region of the top condenser.

It has been found that the polymer formation in the desorption column, in the top condenser of the desorption column, in the top condenser circuit and also in downstream evaporators can be minimized by the addition of polymerization inhibitors.

Preferably, the polymerization inhibitor is added in amounts such that the concentration of the polymerization inhibitor in the liquid condensate stream obtained at the top condenser is from 10 to 500 ppm.

Preferably, the steps E) and F) are further carried out:
E) separating the $C_4$ product stream d1 by extractive distillation using a solvent selective for butadiene into a material stream e1 comprising butadiene and the selective solvent, and a material stream e2 comprising n-butenes;
F) distilling the material stream e1 comprising butadiene and the selective solvent into a material stream f1 substantially comprising the selective solvent, and a material stream f2 comprising butadiene.

Generally, an aqueous refrigerant or an organic solvent is used in the cooling stage Ca).

Preferably, an organic solvent is used in the cooling stage Ca). These generally have a very much higher solvent capacity for the high-boiling byproducts that can lead to deposits and blockages in the plant parts downstream of the ODH reactor than water or alkaline-aqueous solutions. Preferred organic solvents used as refrigerants are aromatic hydrocarbons, for example toluene, o-xylene, m-xylene, p-xylene, diethylbenzenes, triethylbenzenes, diisopropylbenzenes, triisopropylbenzenes and mesitylene (TMB) or mixtures thereof. Particular preference is given to mesitylene.

Embodiments hereinafter are preferred or particularly preferred variants of the inventive method.

Stage Ca) is carried out in a multistage manner in stages Ca1) to Can), preferably in a two-stage manner in two stages Ca1) and Ca2). In this case, particularly preferably, at least a part of the solvent, after passage through the second stage Ca2), is fed as cooling agent to the first stage Ca1).

Stage Cb) generally comprises at least one compression stage Cba) and at least one coolant stage Cbb). Preference is given to at least one cooling stage Cbb), in which the gas that is compressed in the compression stage Cba) is contacted with a cooling agent. Particularly preferably, the cooling agent of the cooling stage Cbb) comprises the same organic solvent that is used as cooling agent in stage Ca). In a particularly preferred variant, at least a part of this cooling agent, after it passes through the at least one cooling stage Cbb, is fed as cooling agent to stage Ca).

Preferably, the stage Cb) comprises a plurality of compression stages Cba1) to Cban) and cooling stages Cbb1) to Cbbn), for example four compression stages Cba1) to Cba4) and four cooling stages Cbb1) to Cbb4).

Preferably, step D) comprises steps Da1), Da2) and Db):
Da1) absorption of the $C_4$ hydrocarbons comprising butadiene and n-butenes in a high-boiling absorbent, wherein an absorbent stream loaded with $C_4$ hydrocarbons and the gas stream d2 are obtained,
Da2) removal of oxygen from the absorbent stream of step Da) that is loaded with $C_4$ hydrocarbons by stripping with a non-condensable gas stream, and
Db) desorption of the $C_4$ hydrocarbons from the loaded absorbent stream, wherein a $C_4$— product gas stream d1 is obtained which substantially comprises $C_4$ hydrocarbons and comprises less than 100 ppm of oxygen.

Preferably, the high-boiling absorbent used in step Da) is an aromatic hydrocarbon solvent, particularly preferably it is the aromatic hydrocarbon solvent used in step Ca), in particular mesitylene. Diethylbenzenes, triethylbenzenes, diisopropylbenzenes and triisopropylbenzenes can also be used.

In an embodiment of the invention, the gas stream d2 present in step Da) is up to at least 30%, preferably up to at least 40%, recirculated to step B). This can be expedient if only a small purge stream has to be ejected from the gas stream d2.

An embodiment of the method according to the invention is shown in FIG. 1 and is described in detail hereinafter.

As feed gas stream, gas mixtures comprising n-butenes (1-butene and/or cis-/trans-2-butene), and isobutene are used. Such a gas mixture can be obtained, for example, by non-oxidative dehydrogenation of n-butane. A fraction can also be used that comprises, as main component, n-butenes (1-butene and cis-/trans-2-butene) and was obtained from the $C_4$ fraction of the naphtha-cracking by separating off butadiene and isobutene. In addition, gas mixtures can be used as starting gas stream that comprise 1-butene, cis-2-butene, trans-2-butene or mixtures thereof, and which were obtained by dimerizing ethylene. In addition, as input gas stream, gas mixtures containing n-butenes can be used which were obtained by fluid catalytic cracking (FCC).

In an embodiment of the method according to the invention, the starting gas mixture comprising n-butenes is obtained by non-oxidative dehydrogenation of n-butane. By the coupling of a non-oxidative catalytic dehydrogenation to the oxidative dehydrogenation of the n-butenes formed, a high yield of butadiene, based on the n-butane used, can be obtained. In the non-oxidative catalytic n-butane dehydrogenation, a gas mixture is obtained which, in addition to butadiene, contains 1-butene, 2-butene and unreacted n-butane minor components. Customary minor components are hydrogen, steam, nitrogen, CO and $CO_2$, methane, ethane, ethene, propane and propene. The composition of the gas mixture leaving the first dehydrogenation zone can vary greatly, depending on the procedure of the dehydrogenation. For instance, when the dehydrogenation is carried out with feed-in of oxygen and additional hydrogen, the product gas mixture can have a comparatively high content of steam and carbon oxides. In the case of procedures without feed-in of oxygen, the product gas mixture of the non-oxidative dehydrogenation has a comparatively high content of hydrogen.

In step B), the feed gas stream comprising the n-butenes and an oxygen-comprising gas are fed into at least one dehydrogenation zone (the ODH reactor A) and the butenes present in the gas mixture are dehydrogenated to butadiene oxidatively in the presence of an oxy dehydrogenation catalyst.

In an embodiment, it is preferred to use an oxygen-comprising gas that comprises more than 10% by volume, preferably more than 15% by volume, and particularly preferably more than 20% by volume, of molecular oxygen. In an embodiment, air is used as oxygen-comprising gas. The upper limit for the content of molecular oxygen in the oxygen-comprising gas is then generally 50% by volume or less, preferably 30% by volume or less, and still more preferably 25% by volume or less. Furthermore, any desired inert gases can be present in the molecular oxygen-comprising gas. As possible inert gases, nitrogen, argon, neon, helium, CO, $CO_2$ and water can be cited. The amount of inert gases in the oxygen-comprising gas is, for nitrogen, generally 90% by volume or less, preferably 85% by volume or less, and still more preferably 80% by volume or less. In the case of components other than nitrogen in the oxygen-comprising gas, the amount is generally 10% by volume or less, preferably 1% by volume or less.

Catalysts suitable for the oxy dehydrogenation are generally based on a Mo—Bi—O-comprising multimetal oxide system which generally additionally comprises iron. Generally, the catalyst system also comprises further additional components such as, for example, potassium, cesium, magnesium, zirconium, chromium, nickel, cobalt, cadmium, tin, lead, germanium, lanthanum, manganese, tungsten, phosphorus, cerium, aluminum or silicon. Iron-containing ferrites have also been proposed as catalysts.

In a preferred embodiment, the multimetal oxide comprises cobalt and/or nickel. In a further preferred embodiment, the multimetal oxide comprises chromium. In a further preferred embodiment, the multimetal oxide comprises manganese.

Examples of Mo—Bi—Fe—O-comprising multimetal oxides are Mo—Bi—Fe—Cr—O or Mo—Bi—Fe—Zr—O-comprising multimetal oxides. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x$+$SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Co_{4.5}Ni_{2.5}Mn_{0.5}K_{0.1}O_x$ and $Mo_{12}BiFe_3Co_{4.5}Ni_{2.5}La_{0.5}K_{0.1}O_x$), U.S. Pat. No. 3,911,039 ($Mo_{12}BiFe_3Co_{4.5}Ni_{2.5}Sn_{0.5}K_{0.1}O_x$), DE-A 25 30 959 and DE-A 24 47 825 ($Mo_{12}BiFe_3Co_{4.5}Ni_{2.5}W_{0.5}K_{0.1}O_x$).

Suitable multimetal oxides and production thereof are additionally described in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x$+$SiO_2$) and DE-A 24 40 329 ($Mo_{12}BiCo_{4.5}Ni_{2.5}Cr_3P_{0.5}K_{0.1}O_x$).

Particularly preferred catalytically active multimetal oxides comprising molybdenum and at least one further metal have the general formula (Ia):

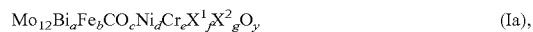

$$Mo_{12}Bi_aFe_bCO_cNi_dCr_eX^1_fX^2_gO_y \qquad (Ia),$$

where $X^1$=Si, Mn and/or Al, $X^2$=Li, Na, K, Cs and/or Rb, $0.2 \le a \le 1$, $0.5 \le b \le 10$, $0 \le c \le 10$, $0 \le d \le 10$, $2 \le c+d \le 10$, $0 \le e \le 2$, $0 \le f \le 10$, $0 \le g \le 0.5$, y= a number which is determined under the precondition of charge neutrality by the valency and frequency of the element different from oxygen in (Ia).

Preference is given to catalysts whose catalytically active oxide mass of the two metals Co and Ni has only Co (d=0). Preferably $X^1$ is Si and/or Mn and $X^2$ is preferably K, Na and/or Cs, particularly preferably $X^2$=K. Particular preference is given to a substantially Cr(VI)-free catalyst.

To carry out the oxidative dehydrogenation at a high overall conversion rate of n-butenes, a gas mixture is preferred that has a molar oxygen:n-butene ratio of at least 0.5. Preferably, an oxygen:n-butene ratio from 0.55 to 10 is employed. To establish this value, the starting gas can be mixed with oxygen or an oxygen-comprising gas and optionally additional inert gas, methane or steam. The resultant oxygen-comprising gas mixture is then fed to the oxy dehydrogenation.

The reaction temperature of the oxy dehydrogenation is generally controlled by a heat-exchange medium which is located around the reaction tubes. As such liquid heat-exchange media, e.g. melts of salts or salt mixtures such as potassium nitrate, potassium nitrite, sodium nitrite and/or sodium nitrate and also melts of metals such as sodium, mercury and alloys of various metals come into consideration. However, ionic liquids or heat carrier oils are also usable. The temperature of the heat-transfer medium is between 220 and 490° C., and preferably between 300 and 450° C., and particularly preferably between 350 and 420° C.

On account of the exothermy of the reactions that proceed, the temperature can be higher in certain sections of the reactor interior during the reaction than those of the heat-exchange medium, and what is termed a hotspot forms. The position and height of the hotspot is established by the reaction conditions, but they can also be regulated by the dilution ratio of the catalyst layer or the throughput of mixed gas. The difference between hotspot temperature and the temperature of the heat-exchange medium is generally between 1 and 150° C., preferably between 10 and 100° C., and particularly preferably between 20 and 80° C. The temperature at the end of the catalyst bed is generally between 0 and 100° C., preferably between 0.1 and 50° C., particularly preferably between 1 and 25° C. above the temperature of the heat-exchange medium.

The oxy dehydrogenation can be carried out in all fixed-bed reactors known from the prior art, such as, for example, in the rack oven, in the fixed-bed tubular reactor or tube-bundle reactor, or in the plate heat exchanger reactor. A tube-bundle reactor is preferred. Preferably, the oxidative dehydrogenation is carried out in fixed-bed tubular reactors or fixed-bed tube-bundle reactors. The reaction tubes are generally fabricated from steel (just as are the other elements of the tube-bundle reactor). The wall thickness of the reaction tubes is typically 1 to 3 mm. The internal diameter thereof is generally (uniformly) 10 to 50 mm, or 15 to 40 mm, frequently 20 to 30 mm. The number of reaction tubes accommodated in the tube-bundle reactor is generally at least 1000, or 3000, or 5000, preferably at least 10 000. Frequently, the number of reaction tubes accommodated in the tube-bundle reactor is 15 000 to 30 000, or up to 40 000, or up to 50 000. The length of the reaction tubes ranges in the usual case to a few meters, typically a reaction tube length is in the range from 1 to 8 m, frequently 2 to 7 m, in many cases 2.5 to 6 m.

In addition, the catalyst layer which is installed in the ODH-reactor A can comprise an individual layer or 2 or more layers. These layers can comprise a pure catalyst, or be diluted with a material that does not react with the starting gas or components of the product gas of the reaction. In addition, the catalyst layers can comprise solid material and/or supported shell catalysts.

The product gas stream 2 leaving the oxidative dehydrogenation, in addition to butadiene, generally comprises still unreacted 1-butene and 2-butene, oxygen and also steam. As minor components, it further generally comprises carbon monoxide, carbon dioxide, inert gases (principally nitrogen), low-boiling hydrocarbons such as methane, ethane, ethene, propane and propene, butane and isobutane, possibly hydrogen and also possibly oxygen-comprising hydrocarbons, termed oxygenates. Oxygenates can be, for example, formaldehyde, furan, acetic acid, maleic anhydride, formic acid, methacrolein, methacrylic acid, crotonaldehyde, crotonic acid, propionic acid, acrylic acid, methyl vinyl ketone, styrene, benzaldehyde, benzoic acid, phthalic anhydride, fluorenone, anthraquinone and butyraldehyde.

The product gas stream 2 at the reactor exit is characterized by a temperature close to the temperature at the end of the catalyst bed. The product gas stream is then brought to a temperature from 150 to 400° C., preferably 160 to 300° C., particularly preferably 170 to 250° C. It is possible to insulate the line through which the product gas stream flows or to use a heat exchanger in order to keep the temperature in the desired range. This heat-exchange system is of any desired type, provided that with this system the temperature of the product gas can be kept at the desired level. As an example of a heat exchanger, spiral heat exchangers, plate heat exchangers, double-tube heat exchangers, multitube heat exchangers, boiler-spiral heat exchangers, boiler-shell heat exchangers, liquid-liquid contact heat exchangers, air-heat exchangers, direct-contact heat exchangers and also finned-tube heat exchangers may be mentioned. Since, while the temperature of the product gas is being set to the desired temperature, a part of the high-boiling byproducts that are present in the product gas can precipitate out, the heat-exchanger system should therefore preferably have two or more heat exchangers. If, in this case, two or more of the provided heat exchangers are arranged in parallel, and thus a distributed cooling of the product gas obtained is permitted in the heat exchangers, the amount of high-boiling byproducts that are deposited in the heat exchangers decreases, and thus the operating time thereof can be prolonged. As an alternative to the abovementioned method, the two or more provided heat exchangers can be arranged in parallel. The product gas is fed to one or more, but not all, heat exchangers which, after a certain operating time, are detached from other heat exchangers. In this method, the cooling can be continued, a part of the heat of reaction recovered, and in parallel thereto, the high-boiling byproducts deposited in one of the heat exchangers can be removed. As a refrigerant mentioned above, a solvent can be used, provided that it is able to dissolve the high-boiling byproducts. Examples are aromatic hydrocarbon solvents such as, e.g. toluene, xylenes, diethylbenzenes, triethylbenzenes, diisopropylbenzenes and triisopropylbenzenes. Particular preference is given to mesitylene. Aqueous solvents can also be used. These can be made either acidic or else alkaline, such as, for example, an aqueous solution of sodium hydroxide.

Then, by cooling and compression, a majority of the high-boiling minor components and the water are separated off from the product gas stream 2. The cooling proceeds by contacting with a refrigerant. This stage is then also termed quench. This quench can comprise only one stage or a plurality of stages (for example B, C in FIG. 1). The product gas stream 2 is therefore brought directly into contact with the organic cooling mediums 3b and 9b, and thereby cooled. As cooling medium, aqueous refrigerants or organic solvents are suitable, preferably aromatic hydrocarbons, particularly preferably toluene, o-xylene, m-xylene, p-xylene or mesitylene, or mixtures thereof. Diethylbenzene, triethylbenzene, diisopropylbenzene and triisopropylbenzene can also be used.

Preference is given to a two-stage quench (comprising the stages B and C as per FIG. 1), i.e. the stage Ca) comprises two cooling stages Ca1) and Ca2), in which the product gas stream 2 is brought into contact with the organic solvent.

Generally, the product gas 2 has a temperature from 100 to 440° C., depending on presence and temperature level of a heat exchanger upstream of the quench B. The product gas is contacted with the cooling medium of organic solvent in the 1st quench stage B. In this case, the cooling medium can be introduced via a nozzle in order to achieve as efficient as possible mixing with the product gas. For the same purpose, internals such as, for example, further nozzles can be introduced in the quench stage, through which internals the product gas and the cooling medium pass together. The refrigerant inlet into the quench is designed in such a manner that blockage by deposits in the region of the refrigerant inlet is minimized.

Generally, the product gas 2 is cooled in the first quench stage B to 5 to 180° C., preferably to 30 to 130° C., and still more preferably to 60 to 110° C. The temperature of the refrigerant medium 3b at the inlet can be generally 25 to 200° C., preferably 40 to 120° C., particularly preferably 50 to 90° C. The pressure in the first quench stage B is not particularly restricted, but is generally 0.01 to 4 bar (gauge), preferably 0.1 to 2 bar (gauge) and particularly preferably 0.2 to 1 bar (gauge). If larger amounts of high-boiling byproducts are present in the product gas, polymerization of high-boiling byproducts and deposits of solids that are caused by high-boiling byproducts in this method section can easily occur. Generally, the quench stage B is designed as a cooling tower. The cooling medium 3b used in the cooling tower is frequently used in circulation. The circuit stream of the cooling medium in liters per hour, based on the mass flow rate of butadiene in grams per hour, can generally be 0.0001 to 5 l/g, preferably 0.001 to 1 l/g, and particularly preferably 0.002 to 0.2 l/g.

The temperature of the cooling medium 3 in the sump can be generally 27 to 210° C., preferably 45 to 130° C., particularly preferably 55 to 95° C. Since the loading of the cooling medium 4 with minor components increases over the course of time, a part of the loaded cooling medium can be taken off from the circulation as purge stream 3a and the amount in circulation can be kept constant by addition of non-loaded cooling medium 6. The ratio of amount in circulation and amount of addition depends on the vapor loading of the product gas and the product gas temperature at the end of the first quench stage.

The product gas stream 4 that is also possibly depleted in minor components can then be fed to a second quench stage C. Therein, it can again be brought into contact with cooling medium 9b.

Generally, the product gas can be cooled up to the gas exit of the second quench stage C to 5 to 100° C., preferably to 15 to 85° C., and still more preferably to 30 to 70° C. The refrigerant can be fed in counterflow to the product gas. In this case, the temperature of the refrigerant medium 9b at the refrigerant inlet can be 5 to 100° C., preferably 15 to 85° C., particularly preferably 30 to 70° C. The pressure in the second quench stage C is not particularly restricted, but is generally 0.01 to 4 bar (gauge), preferably 0.1 to 2 bar (gauge) and particularly preferably 0.2 to 1 bar (gauge). The second quench stage is preferably designed as a cooling tower. The cooling medium 9b used in the cooling tower is frequently used in circulation. The circuit stream of the cooling medium 9b in liters per hour, based on the mass flow rate of butadiene in grams per hour, can be generally 0.0001 to 5 l/g, preferably 0.001 to 1 l/g, and particularly preferably 0.002 to 0.2 l/g.

Depending on temperature, pressure, refrigerant and water content of the product gas 4, condensation of water can occur in the second quench stage C. In this case, an additional aqueous phase 8 can form, which can additionally comprise water-soluble minor components. These can then be taken off in the phase separator D. The temperature of the cooling medium 9 in the sump can be generally 20 to 210° C., preferably 35 to 120° C., particularly preferably 45 to 85° C. Since the loading of the cooling medium 9 with minor components increases over the course of time, a part of the loaded cooing medium can be taken off from the circulation as purge stream 9a, and the amount in circulation can be kept constant by addition of non-loaded cooling medium 10.

In order to achieve the best possible contact between product gas and cooling medium, internals can be present in the second quench stage C. Such internals comprise, for example, bubble-cap, centrifugal and/or sieve trays, columns having structured sheet-metal packings having a specific surface area from 100 to 1000 $m^2/m^3$ such as Mellapak® 250 Y, and randomly packed columns.

The solvent circulations of the two quench stages can be either separate from one another or connected to one another. For instance, the stream 9a can be fed to the stream 3b, or replace it. The desired temperature of the circulation streams can be set via suitable heat exchangers.

In a preferred embodiment of the invention, therefore, the cooling stage Ca) is carried out in a two-stage manner, wherein the solvent loaded with minor components of the second stage Ca2) is conducted into the first stage Ca1). The solvent withdrawn from the second stage Ca2) contains less minor components than the solvent withdrawn from the first stage Ca1).

In order to minimize the entrainment of liquid components from the quench into the off-gas line, suitable structural measures such as, for example, the installation of a demister, can be taken. In addition, high-boiling substances which are not separated off from the product gas can be removed from the product gas by further structural measures such as, for example, further gas scrubbing stages.

A gas stream 5 is obtained which comprises n-butane, 1-butene, 2-butenes, butadiene, possibly oxygen, hydrogen, steam, in small amounts methane, ethane, ethene, propane and propene, isobutane, carbon oxides, inert gases and parts of the solvent used in the quench. In addition, traces of high-boiling components can remain in this gas stream 5, which high-boiling components have not been separated off quantitatively in the quench.

Then, the gas stream b from the cooling stage Ca) which is depleted in high-boiling minor components, is cooled in step Cb) in at least one compression stage Cba) and preferably in at least one cooling stage Cbb) by contacting with an organic solvent as cooling agent.

The product gas stream 5 from the solvent quench is compressed in at least one compression stage E and then further cooled in the cooling apparatus F, wherein at least one condensate stream 14 is formed. A gas stream 12 remains comprising butadiene, 1-butene, 2-butenes, oxygen, steam, possibly low-boiling hydrocarbons such as methane, ethane, ethene, propane and propene, butane and isobutane, possibly carbon oxides and possibly inert gases. In addition, said product gas stream can further comprise traces of high-boiling components.

The compression and cooling of the gas stream 5 can proceed in a single-stage or multistage (n-stage) manner. Generally, in total, compression proceeds from a pressure in the range from 1.0 to 4.0 bar (absolute) to a pressure in the range from 3.5 to 20 bar (absolute). After each compression stage, a cooling stage follows in which the gas stream is cooled to a temperature in the range from 15 to 60° C. The condensate stream can therefore, in the case of multistage compression, also comprise a plurality of streams. The condensate stream comprises large parts of water and the solvent used in the quench. Both streams (aqueous and organic phases) can in addition comprise to a small extent minor components such as low-boilers, $C_4$ hydrocarbons, oxygenates and carbon oxides.

In order to cool stream 11 resulting from compression of stream 5 and/or in order to remove further minor components from the stream 11, the condensed quench solvent can be cooled in a heat exchanger and recirculated as refrigerant to the apparatus F. Since the loading of this cooling medium 13b with minor components increases over the course of time, a part of the loaded cooling medium can be taken off from the circulation (13a) and the amount of cooling medium in circulation can be kept constant by addition of non-loaded solvent (15).

The solvent 15 that is added as cooling medium can be an aqueous refrigerant or an organic solvent. Preference is given to aromatic hydrocarbons, particular preference to toluene, o-xylene, m-xylene, p-xylene, diethylbenzene, triethylbenzene, diisopropylbenzene, triisopropylbenzene, mesitylene or mixtures thereof. Particular preference is given to mesitylene.

The condensate stream 13a can be recirculated to the circuit stream 3b and/or 9b of the quench. As a result, the $C_4$ components absorbed in the condensate stream 13a can again be brought into the gas stream and the yield can thereby be increased.

Suitable compressors are, for example, turbo compressors, rotary piston compressors and reciprocating piston compressors. The compressors can be driven for example, by an electric motor, an expander, or a gas or steam turbine. The input pressure into the first compressor stage is 0.5 to 3 bar absolute, preferably 1 to 2 bar absolute. Typical compression ratios (exit pressure:entry pressure) per compressor stage are, depending on construction type, between 1.5 and 3.0. The cooling of the compressed gas proceeds in refrigerant-flushed heat exchangers or organic quench stages that can be constructed, for example, as tube-bundle, spiral or plate heat exchangers. Suitable refrigerants can be aqueous or the abovementioned organic solvents. As refrigerants in the heat exchangers, in this case, cooling water or heat-transfer oils or organic solvents are used. In addition, preferably air cooling is used for the use of blowers.

The gas stream 12 comprising butadiene, n-butenes, oxygen, low-boiling hydrocarbons (methane, ethane, ethene, propane, propene, n-butane, isobutane), possibly steam, possibly carbon oxides and also possibly inert gases, and possibly traces of minor components, is fed as output stream to the further treatment.

In a step D), non-condensable and low-boiling gas components comprising oxygen, low-boiling hydrocarbons (methane, ethane, ethene, propane, propene), carbon oxides and inert gases are separated off in an absorption column G as gas stream 16 from the process gas stream 12 by absorption of the $C_4$ hydrocarbons in a high-boiling absorbent (21b and/or 26) and subsequent desorption of the $C_4$ hydrocarbons. Preferably, step D), as shown in FIG. 1, comprises the steps Da1), Da2) and Db):

Da1) absorption of the $C_4$ hydrocarbons comprising butadiene and n-butenes in a high-boiling absorbent (21b and/or 26), wherein an absorbent stream loaded with $C_4$ hydrocarbons and the gas stream 16 are obtained, Da2) removal of oxygen from the absorbent stream of step Da1) that is loaded with $C_4$ hydrocarbons by stripping with a non-condensable gas stream 18, wherein an absorbent stream 17 loaded with $C_4$ hydrocarbons is obtained, and Db) desorption of the $C_4$ hydrocarbons from the loaded absorbent stream, wherein a $C_4$- product gas stream 27 is obtained which substantially comprises $C_4$ hydrocarbons.

For this purpose, in the absorption stage G, the gas stream 12 is brought into contact with an absorbent and the $C_4$ hydrocarbons are absorbed in the absorbent, wherein an absorbent loaded with $C_4$ hydrocarbons and an off-gas 16 comprising the remaining gas components are obtained. In a desorption stage H the $C_4$ hydrocarbons are liberated again from the high-boiling absorbent.

The absorption stage can be carried out in any desired suitable absorption column known to those skilled in the art. The absorption can proceed by simply passing the product gas stream through the absorbent. However, it can also proceed in columns or in rotary absorbers. In this case, cocurrent flow, counterflow or cross flow can be employed. Preferably, the absorption is carried out in counterflow. Suitable absorption columns are, e.g., tray columns having bubble-cap, centrifugal and/or sieve trays, columns having structured packings, e.g. sheet metal packings having a specific surface area from 100 to 1000 $m^2/m^3$ such as Mellapak® 250 Y, and randomly packed columns. However, trickling towers and spray towers, graphite block absorbers, surface absorbers such as thick-layer and thin-layer absorbers and also rotary columns, disk scrubbers, cross-spray scrubbers and rotary scrubbers also come into consideration.

In an embodiment, the gas stream 12 comprising butadiene, n-butenes and the low-boiling and non-condensable gas components is fed to an absorption column in the lower region. In the upper region of the absorption column, the high-boiling absorbent (21b and/or 26) is applied.

Inert absorbents used in the absorption stage are generally high-boiling, nonpolar solvents in which the $C_4$ hydrocarbon mixture that is to be separated off has a markedly higher solubility than the remaining gas components that are to be separated off. Suitable absorbents are comparatively nonpolar organic solvents, for example aliphatic $C_8$- to $C_{18}$ alkanes, or aromatic hydrocarbons such as the middle oil fractions of paraffin distillation, toluene or ethers having bulky groups, or mixtures of said solvents, wherein a polar solvent such as 1,2-dimethyl phthalate can be added thereto. Suitable absorbents are, in addition, esters of benzoic acid and phthalic acid having straight-chain $C_1$- to $C_8$ alkanols, and also what are termed heat carrier oils, such as biphenyl and diphenyl ether, the chlorine derivatives thereof and also triarylalkenes. A suitable absorbent is a mixture of biphenyl and diphenyl ether, preferably in the azeotropic composition, for example the commercially available Diphyl®. Frequently, this solvent mixture comprises dimethyl phthalate in an amount from 0.1 to 25% by weight.

In a preferred embodiment, the same solvent is used in the absorption stage Da1) as in the cooling stage Ca).

Preferred absorbents are solvents that have a dissolving power for organic peroxides of at least 1000 ppm (mg of active oxygen/kg of solvent). Preference is given to aromatic hydrocarbons, particularly preferably toluene, o-xylene, p-xylene and mesitylene, or mixtures thereof. Use can also be made of diethylbenzene, triethylbenzene, diisopropylbenzene and triisopropylbenzene.

At the top of the absorption column G, a stream 16 is taken off that substantially comprises oxygen, low-boiling hydrocarbons (methane, ethane, ethene, propane, propene), possibly $C_4$ hydrocarbons (butane, butenes, butadiene), possibly inert gases, possibly carbon oxides and possibly also steam. This material stream can in part be fed to the ODH reactor. By this means, for example the entry stream up to the ODH reactor may be adjusted to the desired Ca hydrocarbon content.

At the sump of the absorption column, by purging with a gas 18, residues of oxygen dissolved in the absorbent may be discharged. The remaining oxygen fraction is to be so small that the stream 27 leaving the desorption column and comprising butane, butene and also butadiene, comprises only a maximum of 100 ppm of oxygen.

The oxygen can be stripped out in step Db) in any desired suitable column known to those skilled in the art. The stripping can be performed by simple passage of non-condensable gases, preferably non-absorbable gases, or only slightly absorbable gases in the absorbent stream 21b and/or 26 such as methane, through the loaded absorption solution. Co-stripped $C_4$ hydrocarbons are scrubbed back into the absorption solution in the upper part of the column G by passing the gas stream back into this absorption column. This can be performed either by pipework of the stripper column, and also by direct assembly of the stripper column beneath the absorber column. Since the pressure in the stripping column part and absorption column part is the same, this can proceed by direct coupling. Suitable stripping columns are, e.g., tray columns having bubble-cap, centrifugal and/or sieve trays, columns having structured packings, e.g. sheet-metal packings having a specific surface area from 100 to 1000 $m^2/m^3$ such as Mellapak® 250 Y, and randomly packed columns. However, trickle towers and spray towers and also rotary columns, disk scrubbers, cross-spray scrubbers and rotary scrubbers also come into consideration. Suitable gases are, for example, nitrogen or methane.

Stream 17 can optionally be cooled or heated and enters into the desorption column H as stream 19. The entry point is generally 0 to 10 theoretical separation plates, preferably 2 to 8 theoretical separation plates, particularly preferably 3 to 5 theoretical separation plates beneath the column head.

The absorbent regenerated in the desorption stage is withdrawn from the desorption column H as stream 20, together with the condensed water. This two-phase mixture can be cooled in a heat exchanger and, as stream 21, be separated in a decanter I into an aqueous stream 21a and an absorbent stream 21b. The absorbent stream 21b is fed back to the absorber column G, while the aqueous stream 21a is evaporated in an evaporator and stream 23 generated thereby. Additionally or as an alternative, additional water (stream 24) can further be evaporated in the evaporator. In addition, also, only a part of the stream 21a can be evaporated, and the non-evaporated part be withdrawn as stream 22 and fed, for example, to wastewater treatment.

Low-boilers such as, for example, ethane or propane, and also high-boiling components such as benzaldehyde, maleic anhydride and phthalic anhydride situated in the process gas stream can accumulate in the absorbent circulation stream. In order to restrict the accumulation, a purge stream 25 can be taken off.

The $C_4$ product gas stream 27 substantially comprising n-butane, n-butenes and butadiene generally comprises 20 to 80% by volume of butadiene, 0 to 80% by volume of n-butane, 0 to 10% by volume of 1-butene and 0 to 50% by volume of 2-butenes, wherein the total amount is 100% by volume. In addition, small amounts of isobutane may be present.

A part of the condensed, principally $C_4$ hydrocarbon-comprising overhead discharge of the desorption column is recirculated as stream 30 to the column head in order to increase the separation efficiency of the column.

The desorption stage H can be carried out in any desired suitable desorption column known to those skilled in the art. The desorption can proceed by lowering the pressure and/or heating the desorption stage. The desorption stage can be heated by supplying a hot medium—as, for example, steam—or by internal vapor which is generated, e.g., by partial evaporation of the absorption solution in the sump of the desorption column.

Suitable desorption columns are, e.g., tray columns having bubble-cap, centrifugal and/or sieve trays, columns having structured packings, e.g. sheet-metal packings having a specific surface area from 100 to 1000 $m^2/m^3$, such as Mellapak® 250 Y, and randomly packed columns. According to the invention, as shown in FIG. 1, a methacrolein-comprising side takeoff stream 31 can be withdrawn from the desorption column H in order to prevent an increase in the concentration of acrolein in the absorbent circuit stream. The side takeoff stream 31 can be either liquid or else gaseous, preferably it is gaseous.

Preferably, the desorption column H has 5 to 30, particularly preferably 10 to 20, theoretical plates. The side takeoff stream 31 is preferably withdrawn here in the lower third of the desorption column. The liquid side takeoff stream 31 generally comprises 0.1 to 2% by weight methacrolein. In addition, it comprises 5 to 15% by weight of water, 0 to 3% by weight of $C_4$ hydrocarbons and 70 to 90% by weight of the absorbent.

The gaseous side takeoff stream 31 generally comprises 1 to 10% by weight of methacrolein. In addition, it comprises 30 to 60% by weight of water, 0 to 6% by weight of $C_4$ hydrocarbons and 30 to 60% by weight of the absorbent.

The gaseous $C_4$ hydrocarbon-comprising stream 29 is recirculated to the compressor E.

Preferably, the polymerization inhibitor is added to the top condenser of the desorption column H together with the stream 27a. Said polymerization inhibitor can be added in solid form, as solution or emulsion. Preferably, it is added as a solution. Particularly preferably, it is added as an aqueous solution. The solution can comprise one or more different stabilizers. Preferred polymerization inhibitors (stabilizers) are selected from the group of unsubstituted and substituted catechols and hydroquinones.

Generally, the polymerization inhibitor is added in an amount such that the concentration thereof in the liquid condensate obtained at the top condenser is from 10 to 500 ppm, preferably 30 to 100 ppm.

Therefore, the concentration of the polymerization inhibitor in stream 28 and in the reflux 30 is 10 to 500 ppm, preferably 30 to 100 ppm.

Preference is given to a mixture of at least one stabilizer from the class of catechols and at least one stabilizer from the class of hydroquinones. Particular preference is given to a mixture of tert-butyl catechol and 4-methoxyphenol.

The liquid stream 28 leaving the top condenser and comprising the $C_4$ hydrocarbons is then evaporated in stage N and the resulting stream 28a is separated by extractive distillation in step E) using a solvent selective for butadiene into a material stream 35 comprising butadiene and the selective solvent, and a material stream 36 comprising butanes and n-butenes.

In an embodiment stream 28 can be scrubbed previously in a liquid-liquid scrubbing with polyalcohols such as ethylene glycol and glycerol or methanol, and the furan present therein can be inpart separated off. In a further embodiment, the stream 28a can be freed in advance from other minor components such as aldehydes in a gas-liquid scrubbing with water.

The extractive distillation can be carried out, for example as described in "Erdöl and Kohle-Erdgas-Petrochemie" [Petroleum and coal—natural gas—petrochemistry], volume 34 (8), pages 343 to 346, or "Ullmanns Enzyklopädie der Technischen Chemie" [Ullmann's encyclopedia of industrial chemistry], volume 9, 4th edition 1975, pages 1 to 18. For this purpose, the $C_4$ product gas stream is contacted with an extraction medium, preferably an N-methylpyrrolidone (NMP)/water mixture, in an extraction zone. The extraction zone is generally designed in the form of a scrubbing column which comprises trays, random packings or structured packings as internals. Said scrubbing column generally has 30 to 70 theoretical separation plates, in order that a sufficiently good separation efficiency is achieved. Preferably, the scrubbing column has a backwash zone in the column head. This backwash zone serves for recovery of the extraction medium present in the gas phase using a liquid hydrocarbon reflux, for which purpose the overhead fraction is condensed in advance. The mass ratio of extraction medium to $C_4$ product gas stream in the feed to the extraction zone is generally 10:1 to 20:1. The extractive distillation is preferably operated at a sump temperature in the range from 100 to 250° C., in particular at a temperature in the range from 110 to 210° C., a head temperature in the range from 10 to 100° C., in particular in the range from 20 to 70° C., and a pressure in the range from 1 to 15 bar, in particular in the range from 3 to 8 bar. The extractive distillation column preferably has 5 to 70 theoretical separation plates.

Suitable extraction media are butyrolactone, nitriles such as acetonitrile, propionitrile, methoxypropionitrile, ketones such as acetone, furfural, N-alkyl substituted lower aliphatic acid amides such as dimethylformamide, diethylformamide, dimethylacetamide, diethylacetamide, N-formylmorpholine, N-alkyl substituted cyclic acid amides (lactams) such as N-alkylpyrrolidones, in particular N-methylpyrrolidone (NMP). Generally, alkyl-substituted lower aliphatic acid amides or N-alkyl substituted cyclic acid amides are used. Dimethylformamide, acetonitrile, furfural and, in particular, NMP are particularly advantageous.

However, mixtures of these extraction media with one another, e.g. of NMP and acetonitrile, mixtures of these extraction media with co-solvents and/or tert-butyl ether, e.g. methyl tert-butyl ether, ethyl tert-butyl ether, propyl tert-butyl ether, n-butyl or isobutyl tert-butyl ether can also be used. NMP is particularly suitable, preferably in an aqueous solution, preferably with 0 to 20% by weight of water, particularly preferably with 7 to 10% by weight of water, in particular with 8.3% by weight of water.

The overhead product stream 36 of the extractive distillation column J substantially comprises butane and butenes and in small amounts butadiene, and is taken off in the gaseous or liquid state. Generally, the stream that substantially comprises n-butane and 2-butene comprises up to 100% by volume of n-butane, 0 to 50% by volume of 2-butene and 0 to 3% by volume further components such as isobutane, isobutene, propane, propene and $C_5^+$ hydrocarbons.

The stream substantially comprising n-butane and 2-butene and possibly methane can be fed in whole or in part or else not into the $C_4$ feed of the ODH reactor. Since the butene isomers of this reflux stream substantially comprise 2-butenes, and 2-butenes are generally oxidatively dehydrogenated more slowly to butadiene than is 1-butene, this reflux stream, before it is fed to the ODH reactor, can be catalytically isomerized. As a result, the isomeric distribution can be adjusted in accordance with the isomeric distribution present in thermodynamic equilibrium. In addition, the stream can be fed to a further workup, in order to separate butanes and butenes from one another and to recirculate the butenes in whole or in part to the oxy dehydrogenation. The stream can also pass into the maleic anhydride production.

In a step F), the butadiene and the material stream comprising selective solvents are separated by distillation into a material stream substantially comprising the selective solvent and a butadiene-comprising material stream.

The material stream 35 obtained at the sump of the extractive distillation column J generally comprises the extraction medium, water, butadiene, and, in small fractions, butenes and butane, and is fed to a distillation column K. Butadiene can be obtained overhead or as a side takeoff. At the sump of the distillation column, an extraction medium and possibly water-comprising material stream 37 occurs, wherein the composition of the extraction medium and water-comprising material stream corresponds to the composition as is added to the extraction. The extraction medium and the water-comprising material stream is preferably returned to the extractive distillation.

If the butadiene is obtained by a side takeoff, the extraction solution thus taken off is transferred to a desorption zone, wherein the butadiene is once again desorbed from the extraction solution and backwashed. The desorption zone can be designed, for example, in the form of a scrubbing column that has 2 to 30, preferably 5 to 20, theoretical plates, and optionally a backwash zone having, for example, 4 theoretical plates. This backwash zone serves for recovery of the extraction medium present in the gas phase using a liquid hydrocarbon reflux, for which purpose the overhead fraction is condensed in advance. As internals, structured packings, trays or random packings are provided. The distillation is preferably carried out at a sump temperature in the range from 100 to 300° C., in particular in the range from 150 to 200° C., and an overhead temperature in the range from 0 to 70° C., in particular in the range from 10 to 50° C. The pressure in the distillation column in this case is preferably in the range from 1 to 10 bar. Generally, in the desorption zone, a pressure reduced in comparison with the extraction zone prevail and/or an elevated temperature.

The valuable product stream 38 obtained at the column head generally comprises 90 to 100% by volume of butadiene, 0 to 10% by volume of 2-butene and 0 to 10% by volume of n-butane and isobutane. For further purification of the butadiene, a further distillation according to the prior art can be carried out.

The claimed technical solution was developed via thermodynamic equilibrium study simulations, and examined in a pilot plant.

This pilot plant comprises the salt bath reactor, the organic quench, the compressor unit and also the $C_4$ absorption/desorption unit. The scale of the pilot plant was selected in such a manner that up-scaling to a large scale plant is possible. The internals of the columns and the refluxes were accordingly selected so as to be representative. The pilot plant can produce between 500 and 1500 grams of butadiene per hour.

COMPARATIVE EXAMPLE

On operation of the plant, polymeric deposits from a methacrolein-butadiene copolymer were found in the topmost column section of desorber column H after 10 days of operation.

In addition, polymeric deposits were also found in the $C_4$ evaporator (N in FIG. 1). The polymer formation at this point was so dominant that the coiled tube evaporator of the plant became blocked.

Example 1

The polymers found have been with high probability formed via a free-radical mechanism. As a countermeasure, a free-radical trap was added to the condenser at the top of the desorber column. By selection of this point of addition, both the condenser and the downstream components were protected from polymers by the free-radical trap. Said free-radical trap distributed itself via the $C_4$ reflux stream 30 into the desorber column and protects the upper column sections which are not protected by an inhibition of the absorbent conducted in circulation. In addition, it also flows together with the stream 28 into the $C_4$ evaporator and also there prevents the formation of polymers. In experiments in the miniplant system with the fluxes tabulated hereinafter, it has been found that fault-free operation was achieved by these measures.

The composition of the individual material streams is shown in table 1.

TABLE 1

| Stream: | | 12 | 16 | 17 | 18 | 19 | 20 | 21 | 21a | 21b |
|---|---|---|---|---|---|---|---|---|---|---|
| Temperature | °C. | 54.1 | 32.4 | 52.9 | 35.0 | 60.0 | 148.0 | 30.0 | 30.0 | 30.0 |
| Pressure | bar | 10.0 | 10.0 | 10.0 | 10.0 | 5.5 | 5.5 | 10.3 | 10.2 | 10.1 |
| Mass flow rate | kg/h | 9.5 | 8.3 | 22.0 | 0.3 | 22.0 | 22.8 | 22.8 | 2.3 | 20.1 |
| BUTANE | % by weight | 3.34 | 0.53 | 1.26 | 0.00 | 1.26 | 0.01 | 0.01 | 0.00 | 0.01 |
| I-BUTANE | | 0.74 | 0.10 | 0.28 | 0.00 | 0.28 | 0.00 | 0.00 | 0.00 | 0.00 |
| 1-BUTENE | | 0.02 | 0.00 | 0.01 | 0.00 | 0.01 | 0.00 | 0.00 | 0.00 | 0.00 |
| C-2-BUTENE | | 0.58 | 0.01 | 0.25 | 0.00 | 0.25 | 0.00 | 0.00 | 0.00 | 0.01 |
| T-2-BUTENE | | 1.36 | 0.02 | 0.59 | 0.00 | 0.59 | 0.01 | 0.01 | 0.00 | 0.01 |
| 1.3-BUTADIENE | | 9.65 | 0.40 | 4.10 | 0.00 | 4.10 | 0.05 | 0.05 | 0.00 | 0.06 |
| Water | | 0.87 | 0.30 | 0.38 | 0.00 | 0.38 | 10.52 | 10.52 | 99.42 | 0.04 |
| ACROLEIN | | 0.17 | 0.13 | 0.68 | 0.00 | 0.68 | 0.67 | 0.67 | 0.23 | 0.72 |
| ACETALDEHYDE | | 0.13 | 0.01 | 0.07 | 0.00 | 0.7 | 0.02 | 0.02 | 0.03 | 0.02 |
| Methacrolein | | 0.28 | 0.25 | 1.01 | 0.00 | 1.01 | 0.98 | 0.98 | 0.18 | 1.08 |
| Mesitylene | | 0.54 | 0.21 | 90.97 | 0.00 | 90.97 | 87.56 | 87.56 | 0.01 | 97.89 |
| Stabilizer | | 0.0000 | 0.0000 | 0.0096 | 0.0000 | 0.0096 | 0.0165 | 0.0165 | 0.0654 | 0.0104 |
| $CO_2$ | | 0.94 | 1.07 | 0.01 | 0.00 | 0.01 | 0.00 | 0.00 | 0.00 | 0.00 |
| CO | | 0.19 | 0.22 | 0.00 | 0.00 | 0.00 | 0.00 | 0.00 | 0.00 | 0.00 |
| $N_2$ | | 74.78 | 89.56 | 0.15 | 100.00 | 0.15 | 0.00 | 0.00 | 0.00 | 0.00 |
| $O_2$ | | 6.16 | 7.11 | 0.00 | 0.00 | 0.00 | 0.00 | 0.00 | 0.00 | 0.00 |
| Others | | 0.26 | 0.08 | 0.23 | 0.00 | 0.23 | 0.15 | 0.15 | 0.07 | 0.16 |

| Stream: | | 22 | 23 | 24 | 25 | 26 | 27 | 27a | 28 | 29 | 30 |
|---|---|---|---|---|---|---|---|---|---|---|---|
| Temperature | °C. | 30 | 157 | 35 | 30 | 35 | 50 | 30 | 17 | 17 | 17 |
| Pressure | bar | 10.2 | 5.6165 | 10.2 | 10.1 | 10 | 5.5 | 5.4 | 5.3 | 5.4 | 5.3 |
| Mass flow rate | kg/h | 0.15 | 2.33 | 0.07 | 0.30 | 0.24 | 3.39 | 0.001 | 1.42 | 0.08 | 1.90 |
| BUTANE | % by weight | 0.00 | 0.00 | 0.00 | 0.01 | 0.00 | 18.68 | 0.00 | 18.86 | 10.46 | 18.86 |
| I-BUTANE | | 0.00 | 0.00 | 0.00 | 0.00 | 0.00 | 4.20 | 0.00 | 4.21 | 3.48 | 4.21 |
| 1-BUTENE | | 0.00 | 0.00 | 0.00 | 0.00 | 0.00 | 0.12 | 0.00 | 0.12 | 0.07 | 0.12 |
| C-2-BUTENE | | 0.00 | 0.00 | 0.00 | 0.01 | 0.00 | 3.69 | 0.00 | 3.74 | 1.61 | 3.74 |
| T-2-BUTENE | | 0.00 | 0.00 | 0.00 | 0.01 | 0.00 | 8.69 | 0.00 | 8.79 | 4.10 | 8.79 |
| 1.3-BUTADIENE | | 0.00 | 0.00 | 0.00 | 0.06 | 0.00 | 60.29 | 0.00 | 60.83 | 35.80 | 60.83 |
| Water | | 99.42 | 99.43 | 100.00 | 0.04 | 0.00 | 0.74 | 10.00 | 0.75 | 0.16 | 0.75 |
| ACROLEIN | | 0.23 | 0.23 | 0.00 | 0.72 | 0.00 | 0.19 | 0.00 | 0.20 | 0.01 | 0.20 |
| ACETALDEHYDE | | 0.03 | 0.03 | 0.00 | 0.02 | 0.00 | 0.80 | 0.00 | 0.80 | 0.71 | 0.80 |
| Methacrolein | | 0.18 | 0.18 | 0.00 | 1.08 | 0.00 | 0.20 | 0.00 | 0.21 | 0.01 | 0.21 |
| Mesitylene | | 0.01 | 0.01 | 0.00 | 97.89 | 100.00 | 0.01 | 0.00 | 0.01 | 0.00 | 0.01 |
| Stabilizer | | 0.0654 | 0.0486 | 0.0000 | 0.0104 | 0.0000 | 0.0000 | 90.0000 | 0.0271 | 0.0000 | 0.0271 |
| $CO_2$ | | 0.00 | 0.00 | 0.00 | 0.00 | 0.00 | 0.06 | 0.00 | 0.04 | 1.03 | 0.04 |
| CO | | 0.00 | 0.00 | 0.00 | 0.00 | 0.00 | 0.00 | 0.00 | 0.00 | 0.00 | 0.00 |
| $N_2$ | | 0.00 | 0.00 | 0.00 | 0.00 | 0.00 | 1.03 | 0.00 | 0.08 | 42.19 | 0.08 |
| $O_2$ | | 0.00 | 0.00 | 0.00 | 0.00 | 0.00 | 0.00 | 0.00 | 0.00 | 0.01 | 0.00 |
| others | | 0.07 | 0.07 | 0.00 | 0.16 | 0.00 | 1.30 | 0.00 | 1.32 | 0.35 | 1.32 |

The invention claimed is:

1. A method for producing butadiene from n-butenes having the steps:

A) providing a feed gas stream a comprising n-butenes;

B) feeding the feed gas stream a comprising n-butenes and an oxygen-comprising gas into at least one oxidative dehydrogenation zone and oxidatively dehydrogenating n-butenes to butadiene, wherein a product gas stream b comprising butadiene, unreacted n-butenes, steam, oxygen, low-boiling hydrocarbons, high-boiling minor components, optionally carbon oxides and optionally inert gases is obtained;

Ca) cooling the product gas stream b by contacting it with a refrigerant and condensing at least a part of the high-boiling minor components;

Cb) compressing the remaining product gas stream b in at least one compression stage, wherein at least one aqueous condensate stream c1 and a gas stream c2 comprising butadiene, n-butenes, steam, oxygen, low-boiling hydrocarbons, optionally carbon oxides and optionally inert gases are obtained;

Da) separating off non-condensable and low-boiling gas components comprising oxygen, low-boiling hydrocarbons, optionally carbon oxides and optionally inert gases as a gas stream d2 from the gas stream c2 by absorbing $C_4$ hydrocarbons comprising butadiene and n-butenes in an absorbent, wherein an absorbent stream loaded with $C_4$ hydrocarbons and the gas stream d2 are obtained, and Db) subsequently desorbing the $C_4$ hydrocarbons from the loaded absorbent stream in a desorption column, wherein a $C_4$ product gas stream d1 is obtained, wherein the desorption column comprises a top condenser located at a head of the column, and wherein a polymerization inhibitor is added in step Db) at the top condenser of the desorption column.

2. The method according to claim 1 further comprising:
E) separating the $C_4$ product gas stream d1 by extractive distillation using a selective solvent for butadiene into a material stream e1 comprising butadiene and the selective solvent, and a material stream e2 comprising n-butenes;
F) distilling the material stream e1 comprising butadiene and the selective solvent into a material stream g1 substantially comprising the selective solvent, and a material stream g2 comprising butadiene.

3. The method according to claim 1, wherein the polymerization inhibitor is added in amounts such that a concentration of the polymerization inhibitor in a liquid condensate stream obtained at the top condenser is from 10 to 1500 ppm.

4. The method according to claim 3, wherein the polymerization inhibitor is a mixture of tert-butyl catechol and 4-methoxyphenol.

5. The method according to claim 1, wherein the polymerization inhibitor is selected from the group consisting of unsubstituted or substituted catechols and hydroquinones.

6. The method according to claim 1, wherein the gas stream d2 that is separated off in step Da) is at least in part recirculated in step B).

7. The method according claim 1, wherein the step Da) comprises the steps Da1) and Da2):
Da1) absorbing the $C_4$ hydrocarbons comprising butadiene and n-butenes in a high-boiling absorbent, wherein the absorbent stream loaded with $C_4$ hydrocarbons and the gas stream d2 are obtained, and
Da2) removing oxygen from the absorbent stream of step Da1) that is loaded with $C_4$ hydrocarbons by stripping with a non-condensable gas stream; and
wherein the $C_4$ product gas stream d1 obtained in step Db) comprises less than 100 ppm of oxygen.

8. The method according to claim 1, wherein the absorbent used in step Da) is an aromatic hydrocarbon solvent.

* * * * *